(12) United States Patent
Mueller et al.

(10) Patent No.: US 7,651,280 B2
(45) Date of Patent: Jan. 26, 2010

(54) COUPLING FOR CONDUITS SEALED IN A RECESS OF A HOUSING

(75) Inventors: Jochen Mueller, Karlsruhe (DE); Karsten Kraiczek, Waldbronn (DE); Bertram Beigel, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 759 days.

(21) Appl. No.: 11/302,873

(22) Filed: Dec. 14, 2005

(65) Prior Publication Data

US 2007/0132230 A1    Jun. 14, 2007

(51) Int. Cl.
  *G02B 6/36* (2006.01)
  *G02B 6/00* (2006.01)
  *G01N 1/10* (2006.01)

(52) U.S. Cl. .............................. 385/92; 385/12; 385/94; 356/246

(58) Field of Classification Search ................... 385/12, 385/13, 125, 92–94; 356/246
See application file for complete search history.

(56) References Cited

U.S. PATENT DOCUMENTS

| | | | | |
|---|---|---|---|---|
| 3,900,245 A | * | 8/1975 | Dyott et al. | 385/51 |
| 4,583,819 A | * | 4/1986 | Duesbury | 385/71 |
| 5,444,807 A | * | 8/1995 | Liu | 385/125 |
| 6,288,783 B1 | * | 9/2001 | Auad | 356/246 |
| 6,542,231 B1 | * | 4/2003 | Garrett | 356/246 |
| 6,603,556 B2 | * | 8/2003 | Belz et al. | 356/440 |

* cited by examiner

*Primary Examiner*—Charlie Peng
(74) *Attorney, Agent, or Firm*—Marc Bobys

(57) ABSTRACT

A coupling for bringing a first conduit in communication with a second conduit. Each of the conduits comprises an end to be coupled and each of the conduits is adapted for conducting a medium. The coupling has a housing and at least one aperture in said housing. The housing is adapted for introducing said first and second conduits into the housing. Furthermore, the coupling comprises a recess in the housing. The recess is adapted for partly receiving the ends of the first and second conduits. The coupling has a seal adapted for sealing the first and second conduits within the recess.

13 Claims, 13 Drawing Sheets

COUPLING FOR CONDUITS SEALED IN A RECESS OF A HOUSING

BACKGROUND ART

1. Field of the Invention

The present invention relates to coupling of conduits.

2. Discussion of the Background Art

Couplings are used for allowing conduits adapted for conducting a medium to communicate. Known are, for example, light guides or fluid conduits for conducting light or a fluid, for example a liquid. A capillary, for example, can serve as a fluid conduit and as a light guide. Flow cells, for example, for analyzing a fluid can comprise a fluid conduit and a light guide. Flow cells can comprise different conduits communicating via one or more connections.

U.S. Pat. No. 6,526,188 B2 and the US 2001/0010747 show a modular flow cell having a high optical throughput, a long optical path length and a small cross-section. The modular flow cell configuration includes remote ports or connections for liquid and light input and liquid and light output.

U.S. Pat. No. 5,444,807 shows a flow-through cell for use in the measurement of chemical properties of small volumes of fluid containing dissolved analytes.

U.S. Pat. No. 5,608,517 discloses a coated flow cell and a method for making the coated flow cell. The flow cell comprises a flow passage, wherein light directed into the flow cell is internally reflected down the flow passage.

U.S. Pat. No. 3,236,602 discloses flow cells and holders therefore, the calorimetric examination of a liquid to determine the quantity of a substance present in the liquid.

U.S. Pat. No. 4,477,186 discloses a photometric cuvette for optical analyses of through-flowing medium, made as a thin and narrow transparent tube requiring minimum sample amounts. Light, substantially parallel to the tube length, is led obliquely into the tube through its wall, is reflected and is led obliquely out through the tube wall to a detector.

EP 008915781 discloses an optical detector cell for determining the presence of a solute in a sample fluid. The optical detector cell includes a sample tube, inlet and outlet means for the sample fluid, and a first and second optical waveguides for passing a beam of light axially through the sample tube.

GB 2193313 A discloses an apparatus and method for measuring the spectral absorbance of fluid samples. The length of the light path through the sample is adjusted to optimize the amount of light absorbed by the sample.

U.S. Pat. No. 6,281,975 B1 shows a bent capillary flow cell with protruding end bulbs coaxial with centreline of an elongated centre cylindrical section of capillary tubing. The bulbs provide a high light throughput entrance window for the cell.

SUMMARY OF THE INVENTION

It is an object of the invention to provide an improved coupling of at least two conduits. The object is solved by the independent claims. Further embodiments are shown by the dependent claims.

According to embodiments of the present invention, a coupling for bringing a first conduit in communication with a second conduit, each conduit comprising an end to be coupled and each conduit being adapted for conducting a medium, is suggested. Embodiments may comprise one or more of the following. The coupling comprises at least one housing part with at least one aperture. The at least one housing part can be part of a housing. The at least one aperture is adapted for introducing and/or admitting at least one of the conduits into the housing and/or housing part. The housing can comprise two apertures, a first aperture for the first conduit and a second aperture for the second conduit. Besides this, the housing comprises a recess. The ends of the first and second conduits can be partly inserted into said recess of the housing.

Furthermore, the at least one aperture of the coupling can comprise a first groove and/or a second groove adapted for partly receiving the first conduit and the second conduit. For example, the first aperture can provide the first groove and the second aperture can provide the second groove. Advantageously, the first and second grooves can guide and fix the first and second conduits. Advantageously, the coupling comprises a seal adapted for sealing said first and second conduits within said recess. Sealing can be understood as any prevention against any side effects, for example, caused by any leakage flow, ingress of dirt, dust, light, and/or alike. The recess can be adapted for surrounding and/or receiving the seal. Advantageously, the seal can surround and fix the first and second conduits within the coupling or better within the recess of the housing of the coupling.

Embodiments can comprise one or more of the following. The recess of the housing of the coupling can comprise a support member. The support member can be adapted for positioning and supporting the ends of the first and second conduits. Advantageously, the ends of the first and second conduits can be positioned and supported additionally to the function of the first and second grooves. Besides this, the support member can protect the ends of the first and second conduits against any contact with the seal. For sealing the first and second conduits, the seal can surround the support member within the recess of the housing of the coupling.

The housing can comprise a bore adapted for coupling at least one of said first and second conduits with a third conduit. Advantageously, the support member can comprise the bore. The bore can be positioned so that the bore is also protected by the support member against any contact with the seal. Furthermore, the bore can be adapted for coupling one or the first and second conduits with a third conduit, for example, for draining or supplying one of the first and second conduits of/with a fluid, for example a liquid. By separating the ends of the first and second conduits and the bore from the seal, at least one of the conduits can be coupled fluidically to the third conduit via the bore.

Embodiments may comprise one or more of the following. The housing can comprise a half shell comprising the recess, the first and second grooves, and the at least one aperture. Advantageously, this half shell can be joined together with an according cover shell. Advantageously, the shapes of the cover shell and the half shell can be adapted to each other, can comprise, for example, according receiving and aligning elements for exactly positioning the half shells to each other. Advantageously, the cover shell can comprise a cover support member adapted for facing the support member of the half shell when the cover shell and the half shell are joined together. The shapes of the support members facing each other can be adapted to the shapes of the first and second conduits, for example, for realizing a press fit for clamping and fixing the ends of the first and second conduits between the support members. The support members joined together can provide a rib adapted for separating the ends of the coupled first and second conduits from the seal. Besides this, the bore of the support member of the half shell can be separated from the seal. By this, the bore can be coupled fluid-tight with at least one of the conduits.

Advantageously the surfaces of the cover shell and the half shell can be coated at least partly. This coating can accomplish an adhesive agent and/or protective coating for the conduits.

Besides this, the cover shell can comprise a first cover groove facing the first groove of the half shell and a second cover groove facing the second groove of the half shell. The grooves facing each other can realize a loose fit for receiving and guiding the first and second conduits. The first cover groove facing the first groove of the half shell realizes the first aperture of the housing. The second cover groove of the cover shell facing the second groove of the half shell realizes the second aperture of the housing. Besides this, the facing grooves can realize a press fit for fixing the first and second conduits within the aperture and within the housing of the coupling. The first aperture provided by the first grooves and the second aperture provided by the second grooves both can lead from the outside of the housing into the recesses inside of the housing of the coupling.

Advantageously, the recesses of the half shell and the cover shell facing each other provide a cavity. The cavity can surround and encapsulate the seal of the coupling. The rib provided by the support members is arranged within the cavity and is surrounded by the seal. By this, each of the first and second conduits can lead through the first and second aperture, realized by the facing grooves, through a hole of the seal to the rib realized by the support members. The rib provides the coupling point of the first and second conduits, sealed fluid-tight by the seal surrounding the rib. Advantageously, each of the conduits can be surrounded by the seal within the cavity for sealing the conduits.

Advantageously, at least one of said shells can comprise a limit stop for positioning the other shell.

Advantageously the at least one of said shells can comprise a floating support member, which allows the at least one inlay part to float in a flat floating direction while facing the counterpart and finally to merge finding a limit stop. This can be done for better mounting and/or for tolerance issues.

Advantageously the at least one of said shells can comprise a floating support member, as described above with a spring mount for compensating different extensions due to different linear thermal expansion coefficient.

Advantageously the floating support members can be realized with an extra part or integrated in one or both of the shells.

Embodiments may comprise one or more of the following. Advantageously, the first conduit can be a wave guide adapted for conducting light and the second conduit can be a capillary adapted for conducting light and/or a fluid. For example, pre-fabricated fused silica capillaries and fibers. Advantageously, such conduits are commercially available and can comprise, for example, a peek-coating or polyimide-coating.

Besides this, the third conduit can be adapted for supplying or draining the capillary with/of the fluid. The coupling point of the first and the second conduits and the third conduit, can be sealed by the seal against any loss of fluid and/or light. The coupling point is provided by the support member within the cavity of the housing. The cavity is provided by the recesses of the shells of the housing.

Advantageously, the cavity can also be provided by additional parts held by the shells.

Advantageously, the wave guide can be inserted into the capillary. By this, for enabling total reflection within the walls of the capillary, any undesired loss of light and/or any stray light can be avoided. In other words, irradiating the span of the capillary being in an optical contact with the housing, for example with an inner surface of the aperture of the housing, and being therefore not suited for said total reflection, can be avoided by inserting the wave guide into the capillary. The wave guide can be arranged coaxially to the end of the capillary for irradiating the fluid or liquid within the capillary. The fluid within the capillary can comprise a liquid sample to be analyzed.

Embodiments may comprise one or more of the following. The seal can comprise a plastic material that was heated, for example, for at least partly plastifying and/or melting. Thereafter, the seal was solidified. By this, the plastic material can be shrunk on the surface of the rib for realizing a fluid-tight contact with the outer surface of the rib. Besides this, the material of the seal can be shrunk on the surfaces of the first and second conduits for realizing such a fluid-tight contact. Besides this, the plastic material can provide a chemical bond with the surfaces of the recess, and/or the surfaces of the first and second conduits. The coupling can comprise said chemical bond between the surfaces and the plastic material. Such a chemical bond can be produced by melting the plastic material at least partly at a contact zone of the surface of the seal. Advantageously, this effect improves the fluid tightness and can consequently be used to reduce the dimension of the seal and consequently the recess surrounding the seal.

The plastic material can be a thermoplastic material, for example, a high performance thermoplastic material or compound, for example, polyetheretherketone (PEEK), flouropolymeres for example perfluoroamines (PFA) or flourinated ethylene-propylene copolymer (FEP), duroplastic material or compound for example polyimide, LCP (liquid crystal polymers), and/or perfluoroamines (PFA), compounds, for example, metal or ceramic filled PEEK, comprising advantageous material properties. For example, a high persistence against aggressive solvents and good sealing properties. Additionally, the plastic material can be coated after forming with a sealing material or a sealing agent, for example, with silicon, rubber, Teflon®, FEP® or alike. Advantageously the plastic material can be pre treated with chemical or physical methods like etching or plasma treating to improve surface energy.

Advantageously, the plastic material expands while heating and shrinks while cooling down. The increased volume of the plastic material leads to an increased pressure within the interfacial area or better the gap between the outer surfaces of the conduits and the inner surface of the aperture. The increased pressure is favorable for enabling the chemical bond. Dependent on the detention time of heating for plastifying and/or melting the plastic material, it can penetrate the surface structure. By this, the plastic material can be bounded between the outer surfaces of the conduits and the inner surface of the aperture. A rough or porous surface improves this effect. During solidifying, the plastic material will be tensed in the surface structure of the inner surface of the aperture. The tensing effect can be improved in a design by which the surface roughness of the material of the inner surface of the aperture is greater than the absolute measurement of the shrinkage of the plastic material. Besides this, the plastic material shrinks on the outer surfaces of the conduits. These effects enable a leak-proof connection of the conduits for pressures, for example, up to 300 bars or higher, via the aperture. Besides this, PEEK is very durable against strong solvents, for example, used for liquid chromatography or high performance liquid chromatography (HPLC) processes and does not cold flowing significantly.

Advantageously, the seal can comprise an elastomeric material, for example, rubber, silicone, polymeric material, and/or alike. The elastomeric material can be pressurized by a pin or alike inserted into a bore of one of the shells, wherein the bore leads into the cavity of the housing. By this, a sealing contact of the elastomeric material with the surfaces of the support members and the first and second conduits can be provided.

In further embodiments, the seal can comprise a low pressure seal comprising, for example, an elastomeric material and a high pressure seal comprising, for example, an adhesive. The low pressure seal can comprise a highly chemically-inert material adapted for being in contact with the fluid within the conduits. The high pressure seal can be adapted for withstanding high pressures. Advantageously, the low pressure seal can be in contact with the fluids and can therefore protect the high pressure seal comprising the adhesive. Any contact of the high pressure seal with the fluids, for example comprising strong solvents, can be avoided.

Further embodiments relate to a fluid analysis system adapted for analyzing a fluid, comprising a flow cell for housing a fluid sample and for exposing said fluid sample to radiation for analysis purposes. The flow cell comprises a capillary adapted for conducting the fluid sample, a light path comprising the capillary, a first and a second light guide adapted for conducting the light into and out of the flow cell. Besides this, the flow cell comprises a supplying conduit adapted for conducting the fluid sample into the capillary. For sealing the capillary, the supplying conduit, and the light guides, the flow cell comprises at least one coupling for bringing the capillary in communication with the light guide. Advantageously, the coupling can reduce any undesired dead volume of the flow cell. Furthermore, relative long path length can be realized.

Embodiments may comprise one or more of the following. The coupling can comprise a housing with at least one aperture. The at least one aperture is adapted for introducing the capillary and the light guide into the housing. The housing can comprise two apertures, one for the capillary and one for the light guide. Besides this, the housing comprises a recess. The ends of the capillary and the light guide can be partly inserted into said recess of the housing. Advantageously, the coupling can comprise a seal adapted for sealing the capillary and the light guide within the recess. The recess can be adapted for surrounding and/or receiving the seal. Advantageously, the seal can surround and fix the capillary and the light guide within the coupling or better within the recess of the housing of the coupling.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIGS. 6 and 7 show 3-dimensional detailed top front side views of a half shell of the partly assembled coupling of FIG. 4, wherein FIG. 6 shows the half shell together with the capillary and the wave guide inserted into grooves of the half shell, FIG. 10 shows a detailed 3-dimensional grid view of the coupling of FIG. 5, FIG. 11 shows a detailed grid side view of the coupling of FIG. 5.

DETAILED DESCRIPTION OF THE PREFERRED EMBODIMENT

Figure 1:
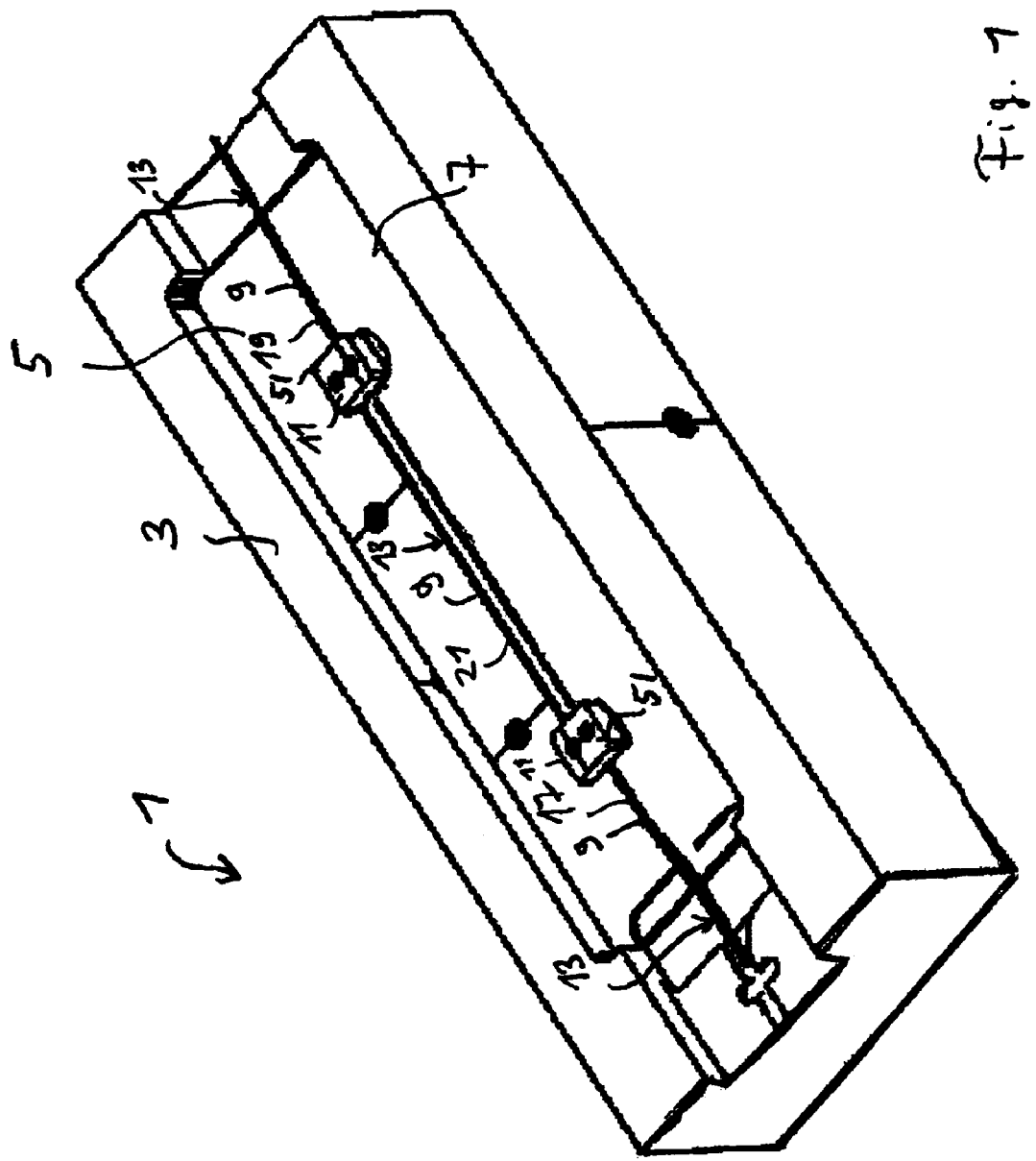
FIG. 1 shows a 3-dimensional top side front view of a flow cell with a cover, wherein the flow cell comprises conduits coupled by couplings.

FIG. 1 shows a flow cell 1 comprising a cover 3 surrounding a supporting plate 5. The cover 3 of the flow cell 1 comprises a window 7 whereas the supporting plate 5 of the flow cell 1 is visible in FIG. 1. The supporting plate 5 supports conduits 9 and couplings 11 adapted for connecting the conduits 9. The conduits 9 of the flow cell 1 comprise a light path 13. The light path 13 is adapted for conducting light, in particular for conducting light though a liquid sample, for irradiating the sample with the light.

The light path comprises an inlet wave guide 17 and an outlet wave guide 19. The inlet wave guide 17 is coupled to a not visible light source, for example, a laser or a lamp. The outlet wave guide 19 is coupled to a not shown detector adapted for detecting the amount of light conducted within the outlet wave guide 19. The wave guides 17 and/or 19 can also be an optical element like a window, glass rod, and/or alike. The inlet wave guide 17 is adapted for conducting the light to the fluid sample via the coupling 11. The couplings 11 are adapted for coupling the inlet wave guide 17 of the flow cell 1 to a capillary 21. The capillary 21 is adapted for conducting the liquid fluid sample and is adapted for conducting the light within the fluid sample. The conduits 9, namely the wave guides 17, 19 and the capillary 21 are supported by the supporting plate 5 of the flow cell 1. The supporting plate 5 is adapted for fixing, aligning, positioning, and protecting the functional elements of the flow cell 1.

Figure 2:
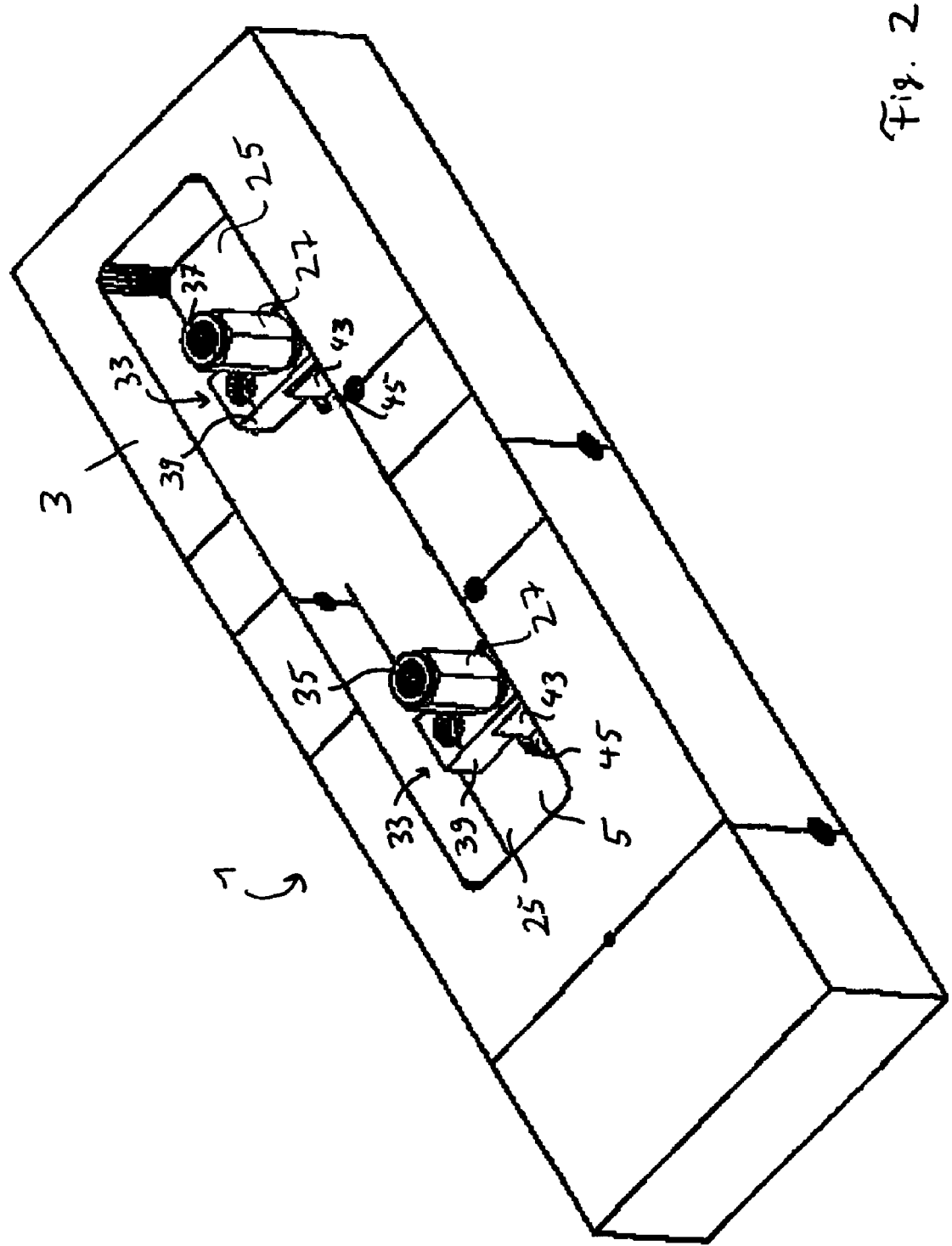
FIG. 2 shows a 3-dimensional bottom side front view of the flow cell of FIG. 1.

FIG. 2 shows a 3-dimensional bottom side front view of the flow cell 1 showing the cover 3 comprising a bottom window 25. For analyzing a solute, the flow cell 1 can be connected via the bottom window 25. More precisely, the bottom window 25 is adapted for allowing access to fittings 27 adapted for draining and/or supplying the flow cell 1 of/with the fluid sample to be analyzed. Therefore, the fittings 27 can be connected with not shown fluid conduits, for example, connected to a waste and a fluid source, for example, a pump. The cover 3 of the flow cell 1 can be adapted for connecting the flow cell 1 with the not shown light source and the not shown detectors.

Figure 3:
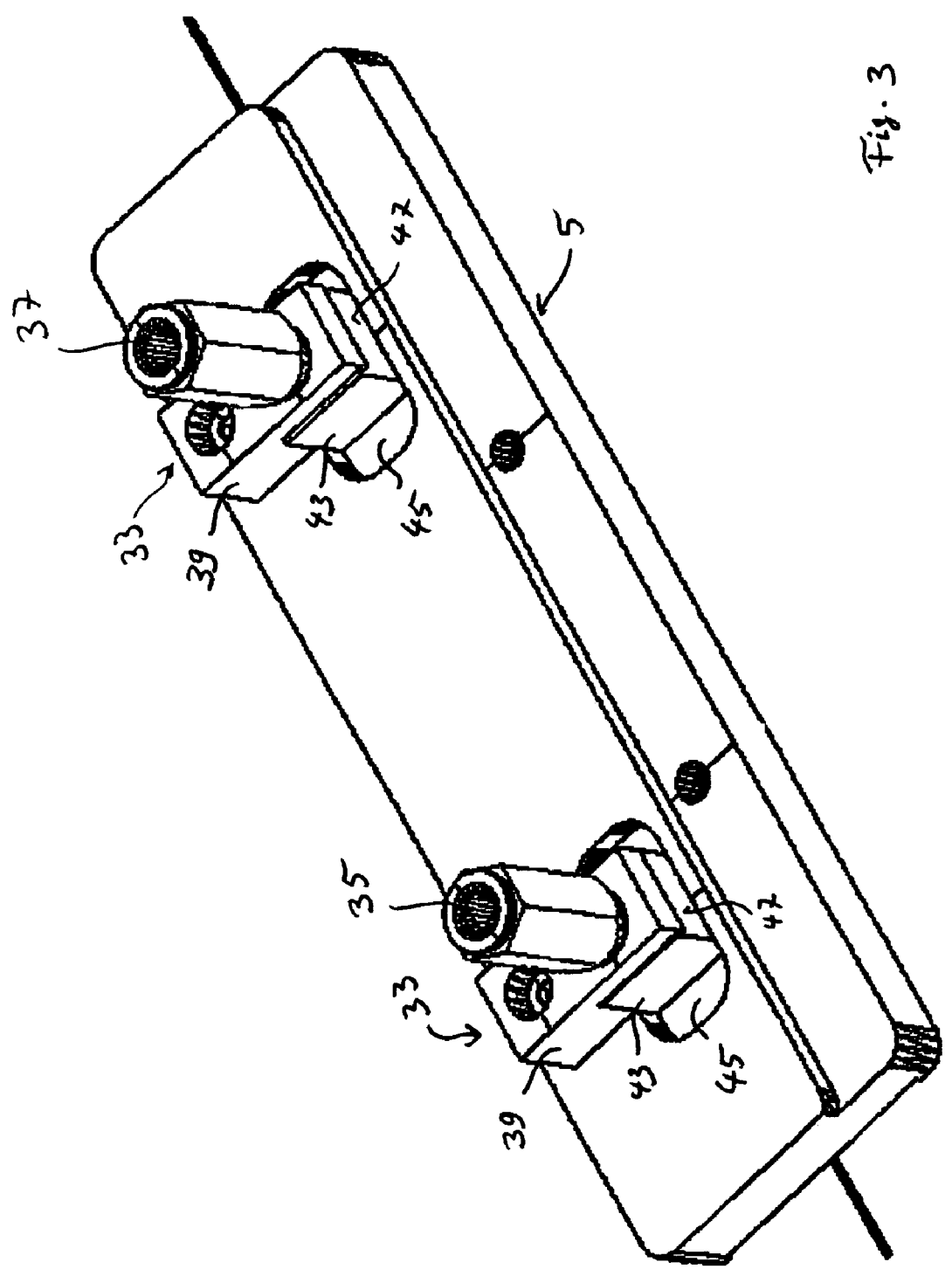
FIG. 3 shows a 3-dimensional bottom side front view of a supporting plate of the flow cell of the FIGS. 1 and 2.

FIG. 3 shows a 3-dimensional bottom side front view of the supporting plate 5 of the flow cell 1. Each of the couplings 11, not visible in FIG. 3, are part of an assembly 33. The flow cell 1 comprises a measuring path comprising two of the assemblies 33, wherein one of the assemblies realizes an inlet 35 for the fluid to be analyzed and the other assembly realizes an outlet 37.

Figure 4:
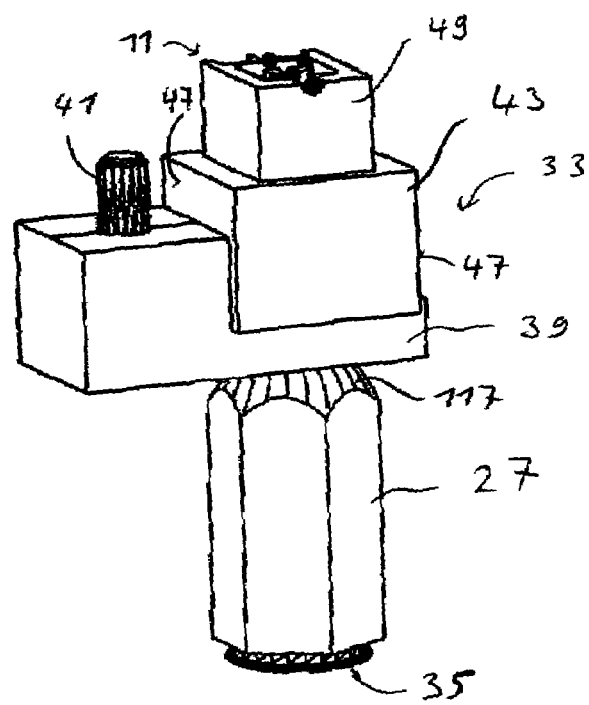
FIG. 4 shows a 3-dimensional side front top view of an assembly comprising a fitting, a plug-in part, and a partly assembled coupling.

FIG. 4 shows a 3-dimensional side front top view of one assembly 33 of the flow cell 1. The assembly 33 comprises the fitting 27, for example, realizing an inlet 35 for the flow cell 1. The fitting 27 is fixed with a plug-in part 39, for example, by a not visible thread. The plug-in part 39 comprises an aligning pin 41 adapted for aligning and/or positioning the assembly 33 relative to the supporting plate 5 of the flow cell 1. Therefore, the supporting plate 5 comprises, not visible in FIG. 3, bores adapted for receiving the pin 41 of the plug-in part 39. The plug-in part 39 is assembled with a cube 43. The supporting plate 5 of the flow cell 1 comprises recesses, wherein the recesses 45 are adapted for receiving and/or aligning the cubes 43 of the assemblies 33. Each of the cubes 43 comprises two parallel aligning surfaces 47. The aligning surfaces 47 are adapted for realizing a fit with inner surfaces of the recesses 45 of the supporting plate 5, for example, a loose fit or a press fit. By this, the assembly 33 can be positioned relatively exactly to the supporting plate 5 by the aligning surfaces 47 of the cube 43 and the pin 41 of the plug-in part 39. The pin 41 can be inserted into the not visible bore of the supporting plate 5 until the surface of the plug-in part 39 adjacent to the pin 41 is limited at the outer surface of the supporting plate 5. The cube 43 of the assembly 33 is fixed with a half shell 49 of the coupling 11. The functions of the cube 43 and the half shell 49 also can be realized as an integral part.

Figure 5:
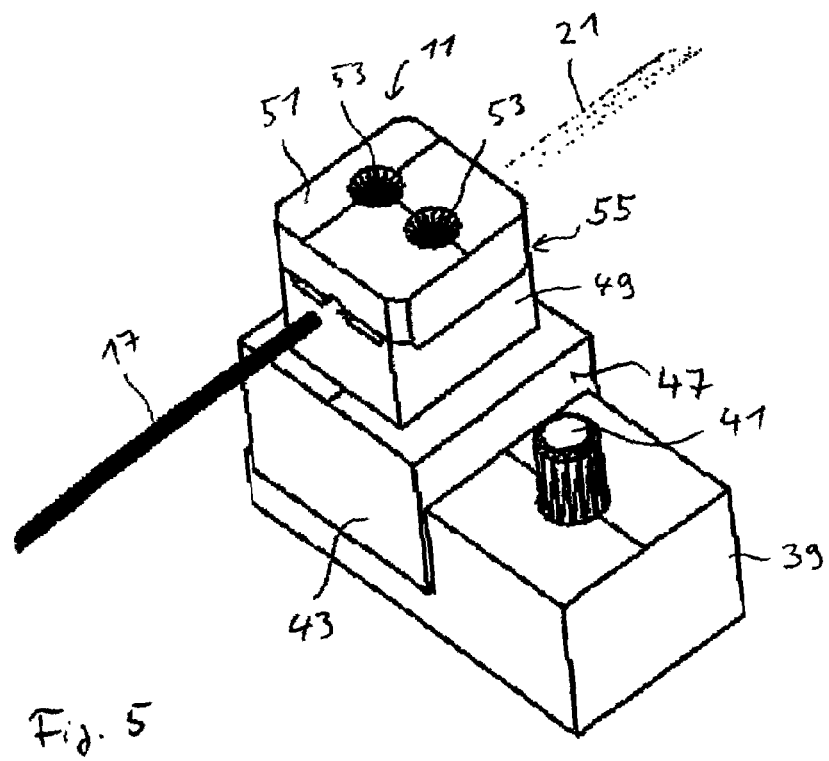
FIG. 5 shows a 3-dimensional top side front view of the assembly of FIG. 4, but without the fitting and with the completely assembled coupling, wherein the coupling is coupled to a capillary and to a wave guide.

FIG. 5 shows a 3-dimensional top side front view of the assembly 33 of FIG. 4, but without the fitting 27. FIG. 5 shows the coupling 11 completely assembled together with a wave guide 17 and a capillary 21. For connecting the wave guide 17 and the capillary 21, the half shell 49 is covered by a cover shell 51. The coupling 11 comprising the half shell 49 and the cover shell 51 comprises substantially a cubical outer shape. The cover shell 51 comprises two holes 53, for example, for filling the inside of the coupling 11 with a seal, not visible in FIG. 5. The half shell 49 and the cover shell 51 of the coupling 11 realize a housing 55 of the coupling 11. The housing parts, namely the half shell 49 and the cover shell 51 of the housing 55 can protect and fix the ends of the wave guide 17 and the capillary 21 and can surround the seal.

Advantageously the surfaces of the cover shell and/or the half shell can be coated at least partly. This coating can accomplish an adhesive agent and/or protective coating for the conduits. The coating is exemplarily indicated in FIG. 8 by some dots 56.

Figure 6:
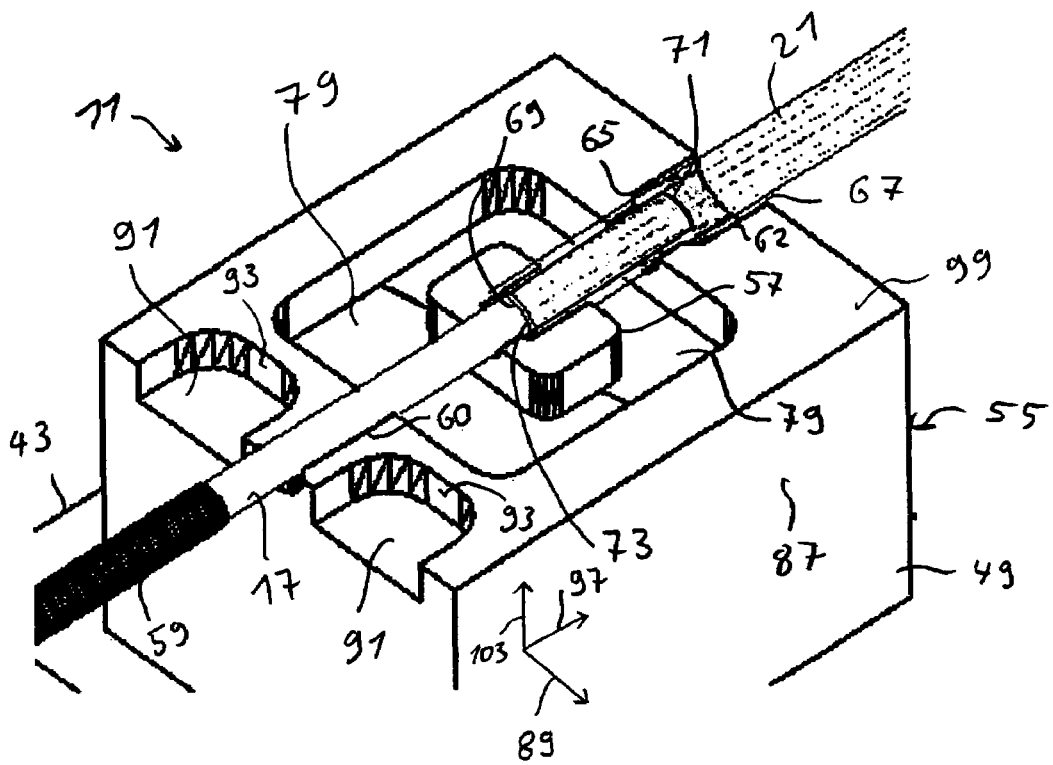
Figure 7:
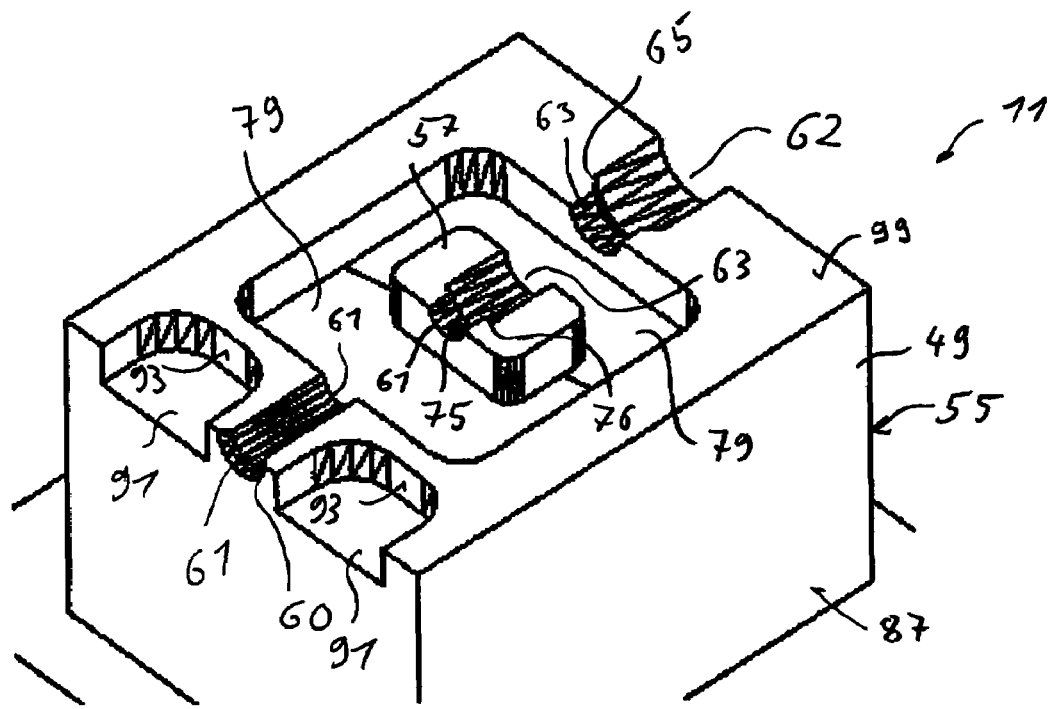

FIGS. 6 and 7 show detailed 3-dimensional views of the half shell 49 of the coupling 11 of the flow cell 1.

Figure 8:
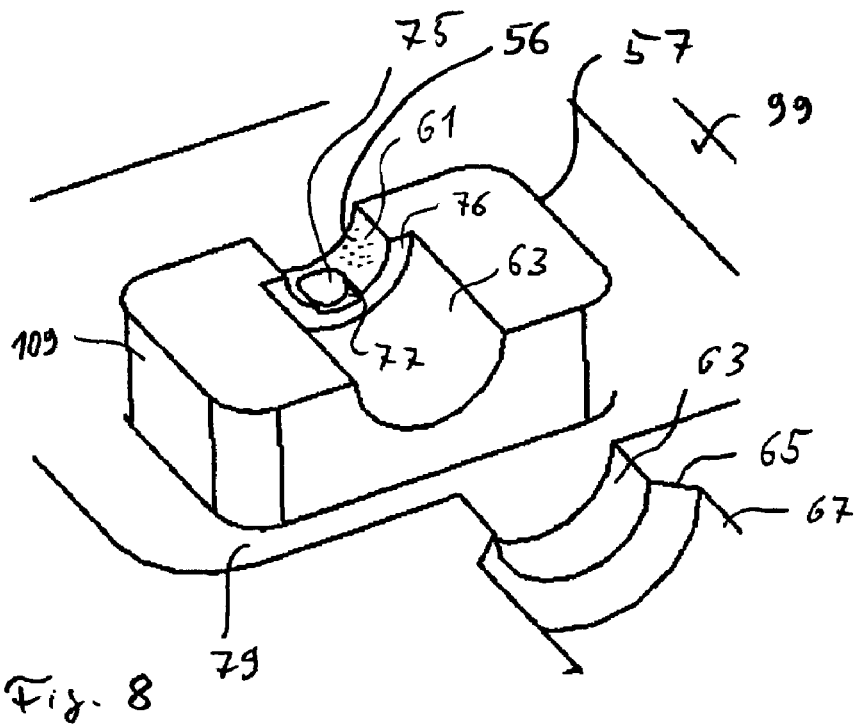
FIG. 8 shows a detailed view of a support member of the half shell of FIG. 7.

FIG. 8 shows a detailed view of a support member 57 of the half shell 49.

Figure 9:
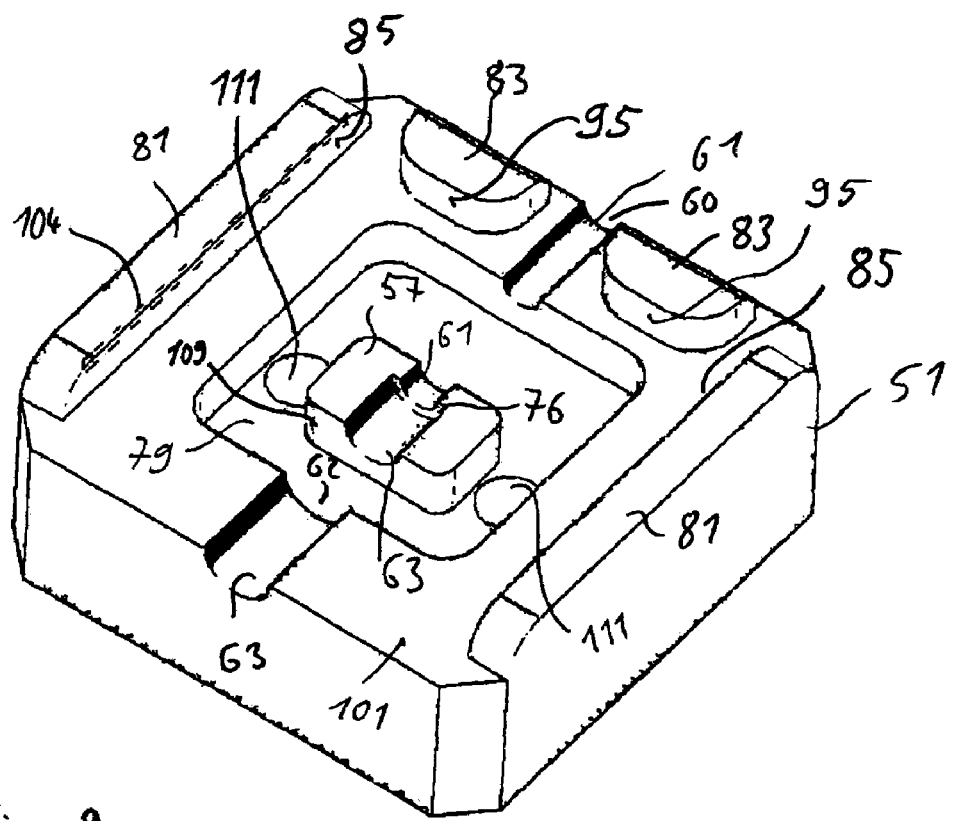
FIG. 9 shows a 3-dimensional inner view of a cover shell adapted for fitting together with the half shell of FIG. 6.
Figure 70:
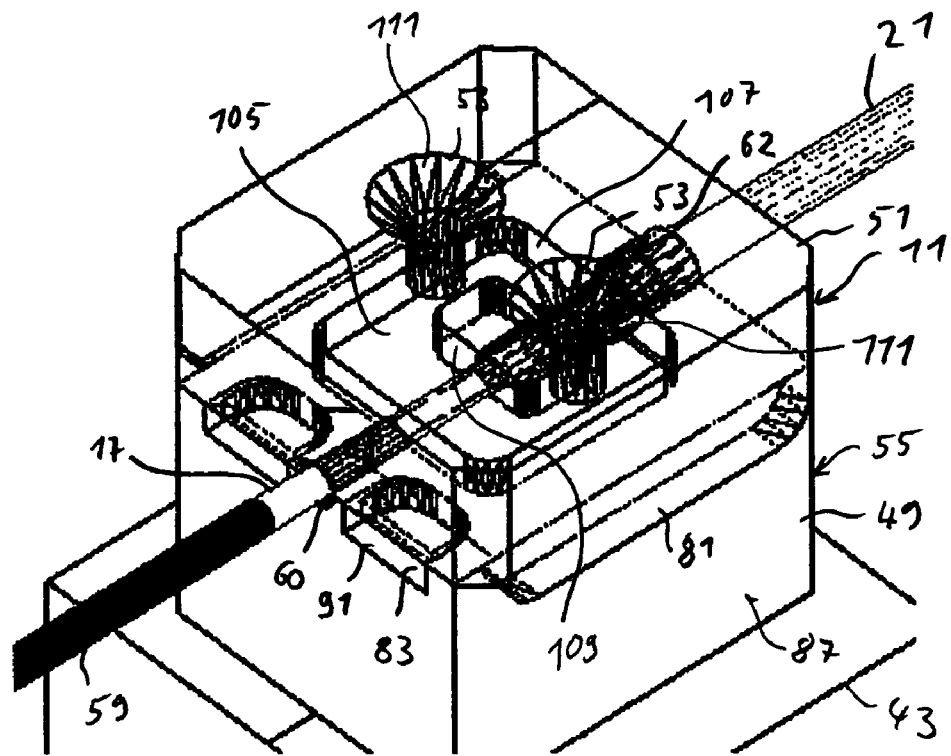
Figure 71:
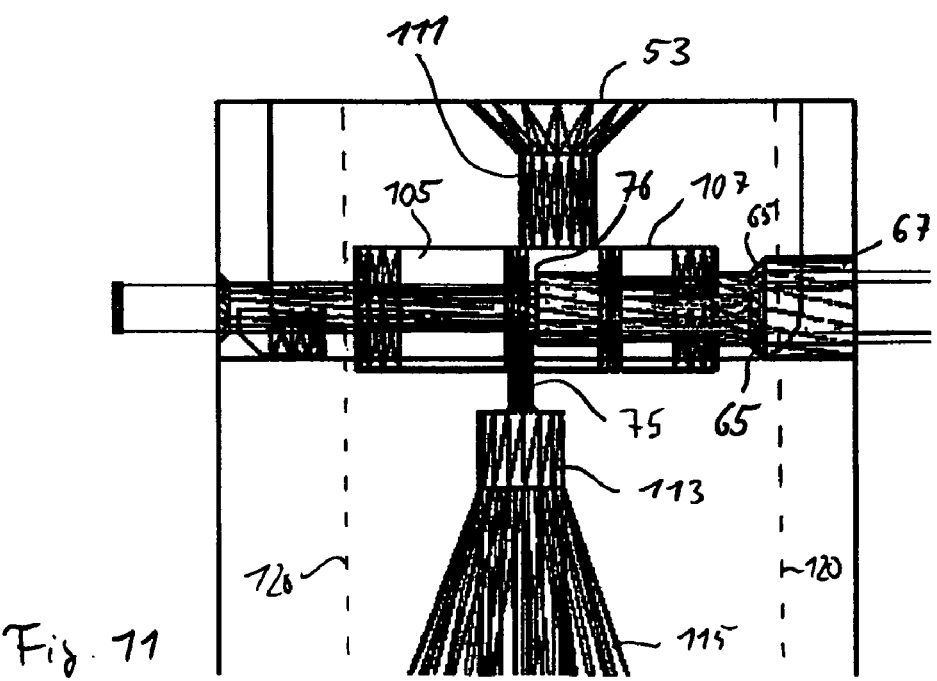

FIG. 9 shows a 3-dimensional inner view of the cover shell 51 of the coupling 11. In the following, the functionality of the half shell 49 and the cover shell 51 of the coupling 11 is described by referring to the FIG. 6-9.

As shown in the FIGS. 6 and 7, the half shell 49 of the housing 55 of the coupling 11 is adapted for receiving the capillary 21 and the wave guide 17. The wave guide 17 can comprise a cover 59 adapted for at least partly covering and protecting the wave guide 17. As shown in FIG. 7, the half shell 49 comprises a first aperture 60 comprising a first groove 61 adapted for receiving the wave guide 17 and a second aperture 62 comprising a second groove 63 adapted for receiving the capillary 21. The second groove 63 can comprise a step 65 enlarging the inner diameter of the second groove towards the outside of the half shell 49 of the housing 55. The smaller inner diameter of the second groove 63 is adapted exactly to the outer diameter of the capillary 21 for fixing and supporting the capillary 21. As shown in FIG. 6, the groove 63 between the outside of the half shell 49 of the housing 55 and the step 65 provides a gap 67. The gap 67 is filled with air and guarantees an optical insulation between the housing 55 and the capillary 21. The wave guide 17 is inserted into an opening 69 of the capillary 21.

The wave guide 17 is inserted so deeply into the opening 69 of the capillary 21, that an optical outlet 71 of the wave guide 17 lies behind the step 65 of the second groove 63, for example, in the span of the second groove 63 of the gap 67. Because of the optical insulation of the gap 67, any loss of light caused by an optical contact of the outer surface of the capillary 21 and the half shell 49 of the housing 55 can be avoided.

The optical outlet 71 of the wave guide 17 can irradiate a fluid sample conducted within an inner tube 73 of the capillary 21. The outer diameter of the wave guide 17 is smaller than the inner diameter of the inner tube 73. Therefore, liquid can be conducted through the inner tube 73 of the capillary 21 in spite of the presence of the inserted wave guide 17.

For conducting the liquid sample into or out of the capillary 21, the support member 57 of the half shell 49 comprises a bore 75, as shown in FIG. 8. The bore 75 can be coupled with a fluid conduit adapted for draining or supplying the capillary 21 of/with the fluid sample. The bore 75 leads into the groove 61 of the support member 57 of the half shell 49. In the middle of the half shell 49, the first groove 61 and the second groove 63 of the support members 57 of the shells 49, 51 face each other and provide a step 76. The step 76 reduces the outer diameter of the second groove 63 adapted to the outer diameter of the capillary 21 to the inner diameter of the first groove 61 adapted to the outer diameter of the wave guide 17. The bore 75 is connected to the second groove 63 by a fluid groove 77 as shown in FIG. 8. The end of the capillary 21 comprising the opening 69 is inserted adjacent to the step 76 into the groove 63. For realizing a fluidic connection between the bore 75 and the opening 69 of the capillary 21, the first groove 61 comprises the fluid groove 77. In other words, the fluid sample can flow through the bore 75 through the fluid groove 77 along the outer surface of the wave guide 17 into the opening 69 of the capillary 21. Within the capillary 21 the fluid sample can flow between the outer surface of the wave guide 17 and the inner surface of the inner tube 73 to the optical outlet 71 of the wave guide 17. At the optical outlet 71 of the wave guide 17, the fluid sample can be irradiated while flowing within the inner tube 73 of the capillary 21.

As illustrated in the FIG. 6-8, the first and second grooves 61, 63 are interrupted by a recess 79. The recess 79 can be adapted for receiving an according seal.

The cover shell 51, as shown in FIG. 9, is designed substantially symmetrically to the half shell 49. Therefore, the cover shell 51 also comprises the apertures 60 and 62 of the housing 55 comprising a first groove 61 and a second groove 63 adapted for guiding, fixing and/or receiving the wave guide 17 and the capillary 21. Besides this, the cover shell 51 also comprises a recess 79 according to the recess 79 of the half shell 49, and also comprises a support member 57. The diameter of the second groove 63 of the support member 57 of the cover shell 55 in the middle of the cover shell 51 between a step 76 and the recess 79 is adapted to the outer diameter of the capillary 21. At the step 76, the second groove 63 ends and leads into the first groove 61, wherein the diameter of the second groove 63 is reduced to the diameter of the first groove 61 adapted to the diameter of the light guide 17. The steps 76 of the half shell 49 and the cover shell 51 can realize a limit stop adapted for limiting the end of the capillary 21.

The cover shell 51 can comprise aligning elements 81 and 83. The aligning elements 81 comprise inner surfaces 85 adapted for joining together with outer surfaces 87 of the half shell 49. The surfaces 85, 87 of the half shell 49 and cover shell 51 can realize limit stops for positioning the half shell 49 and the cover shell 51 in direction of a first axis, as indicated with an arrow 89 in FIG. 6. The half shell 49 can comprise at least one aligning recess 91, for example, two aligning recesses 91.

The aligning recesses 91 of the half shell 49 are adapted for receiving the aligning elements 83 of the cover shell 51. For aligning the half shell 49 and the cover shell 51, the recesses 91 of the half shell 49 comprises surfaces 93 adapted for realizing a limit stop together with outer surfaces 95 of the aligning elements 83 of the cover shell 51. The second axis is indicated in FIG. 6 with an arrow 97.

Finally, the half shell 49 comprises a surface 99 adapted for realizing a limit stop together with a surface 101 of the cover shell 51. The surfaces 99 and 101 are adapted for aligning the half shell 49 and cover shell 51 in direction of a third axis as indicated with an arrow 103. The aligning surfaces 99, 101 of the shells 49, 51 and the surfaces 93, 95 of the recesses 91 and of the aligning elements 83, and the surfaces 87, 85 of the half shell 49 and of the aligning elements 81 of the cover shell 51 are rectangular to each other. By this, the half shell and the cover shell can be aligned in direction of three axes as indicated by the arrows 89, 97, 103. By this, the half shell 49 and the cover shell 51 can be positioned to each other without any degree of freedom remaining.

Advantageously, the aligning elements 81 and/or 83 can comprise a phase 104 (exemplarily indicated in FIG. 8 with dashed lines) adapted for positioning the shells 49 and 51 relative to each other while joining them together.

The shells 49 and/or 51 can be supported in a floating manner, for example, by a loose fit, wherein the shells 49 and/or 51 can be inserted into according recesses. Advantageously, the shells 49 and 51 can snap in the correct position. Advantageously, this enables a wider range of the allowable limits and an improved mounting of the flow cell 1.

FIG. 10 shows a detailed 3-dimensional grid view of the coupling 11 of FIG. 5.

FIG. 11 shows a detailed grid side view of the coupling 11 of FIG. 5.

The grid views of FIGS. 10 and 11 show visible and not visible details of the coupling 11. All aligning surfaces 87, 93, 99 of the half shell 49 are in contact with the according aligning surfaces 85, 95, 101 of the cover shell 51. It can be seen that the recesses 79 of the half shell 49 and the cover shell 51 faces each other and provide a cavity 105 of the housing 55 of the coupling 11. The cavity 105 is adapted for receiving a seal 107. The seal 107 partly surrounds the outer surfaces of the wave guide 17 and the capillary 21 for sealing them. Besides this, the seal 107 surrounds a rib 109, wherein the rib is provided by the support members 57 of the half shell 49 and the cover shell 51 facing each other. The rib 109 is adapted for receiving the wave guide 17 and the capillary 21 and is adapted for protecting the coupling point or better the interface between the wave guide 17 and the capillary 21 against any contact with the seal. Besides this, the rib 109 is adapted for positioning the ends of the wave guide 17 and the capillary 21 within the housing 55 of the coupling 11. The cover shell 51 can comprise two bores 111 with conically shaped ends directed towards the outside of the housing 55. The bores 111 can be adapted for filling the seal 107 into the cavity 105.

Figure 12:
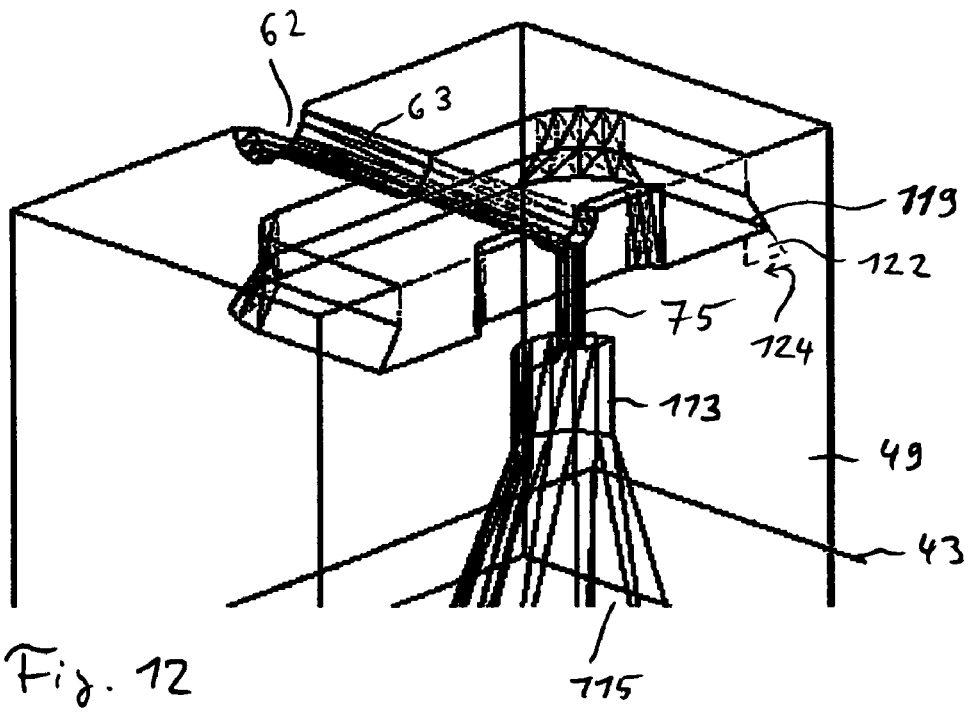
FIG. 12 shows a 3-dimensional sectional grid view of the coupling of FIG. 5.

FIG. 12 shows a sectional grid view of the half shell 49 of the coupling of FIG. 5. As seen in FIGS. 11 and 12, the bore 75 adapted for coupling the capillary 21 to a third fluid conduit leads rectangular into the capillary 21 via the first groove 61 and the fluid groove 77 of the support member 57 of the half shell 49. The bore 75 leads upstream of the capillary 21 into a threaded bore 113 leading into a conically shaped opening 115. The threaded bore 113 is adapted for receiving an according thread of the fitting 27. The conically shaped opening 115 is adapted to a conically shaped outer surface 117 of the fitting 27, as shown in FIG. 4. The conically shaped outer surface 117 can be brought in a sealing contact with the conically shaped opening 115 by screwing the fitting 27 into the threaded bore 113 of the half shell 49. The fitting 27 can be coupled to a not shown third fluid conduit.

FIG. 12 shows a variation of the recess 45 of the half shell 49, wherein the recess 45 comprises an undercut 119. The undercut 119 can comprise an additional recess 122 as exemplarily indicated with dashed lines in FIG. 12. For improving the sealing, the plastic material can shrink on the surface of the recess 122. The direction of the resulting shrinking forces is indicated by an arrow 124.

Figure 13:
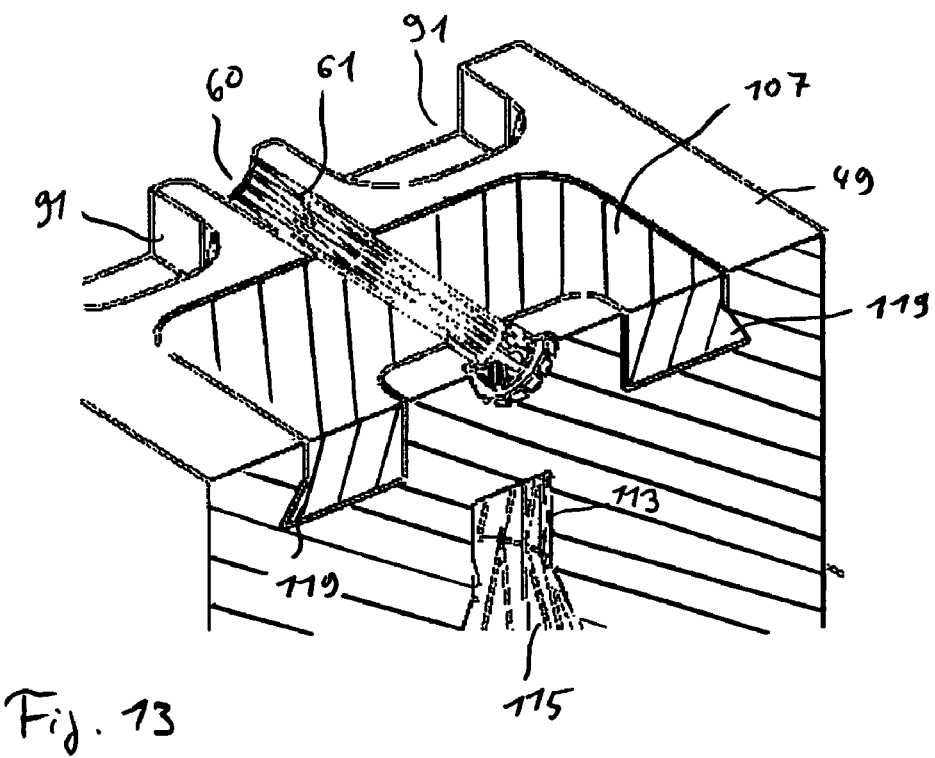
FIG. 13 shows a 3-dimensional sectional view of the coupling of FIG. 5 comprising two cutting planes.

FIG. 13 shows a sectional view of the coupling of FIG. 12, but comprising two cutting planes. As shown in FIG. 13, the recess 45 is filled with the seal 107. The seal 107 is fixed in a form-fitting manner within the recess 45 due to the undercut 119. For this purpose, for example, the seal 107 can comprise a plastic material that was melted for filling it into the cavity 105 of the housing 55 through the bores 111 of the cover shell 51. By this, the seal 107 can provide a chemical bond with the surface of the cavity 105 and with the outer surfaces of the rib 109 and with the outer surfaces of the wave guide 17 and the capillary 21. By this, the conduits leading through the coupling 111 can be sealed completely against any loss of fluid.

The coupling 11 couples three branches, wherein the wave guide 17 realizes a first branch, the capillary 21 realizes a second branch and the bore 75 leading into the fitting 27 realizes a third branch. The first branch is adapted for conducting light, the second branch is adapted for conducting light and/or a fluid, for example, a liquid, and the third branch is adapted for conducting the fluid or the liquid.

Figure 14:
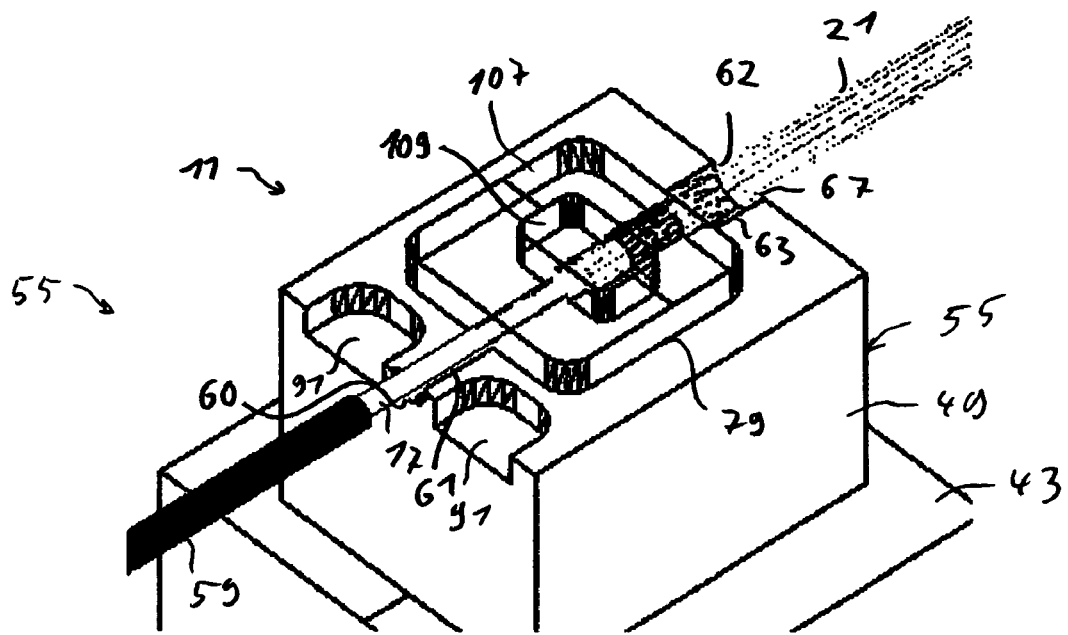
FIG. 14 shows the half shell of FIG. 6, but additionally with a seal comprising a plastic material.

FIG. 14 shows the half shell 49 as shown in FIG. 6, but additionally with the seal 107. For inserting or filling the seal 107 into the cavity 105 of the housing 55, the plastic material can be melted by heating. After filling the plastic material into the cavity, it can be cooled down to ambient temperature. By this, the plastic material can shrink on the surfaces of the wave guide 17 and the capillary 21 and the rib 109. In further embodiments, the seal 107 can be provided by a not shown mold. The already produced seal 107 can be inserted as a preassembly together with the capillary 21 and the wave guide 17 into the recess 45 of the half shell 49 as shown in FIG. 14. Thereafter, the cover shell 51 can be fit together with the half shell 49. The shells can be fixed together, for example, by screws (just indicated in FIG. 11 with dashed lines 120). Furthermore, the seal 107, the wave guide 17, and the capillary 21 can be inserted into the housing 55. Thereafter, the housing 55 can be heated together with the conduits 17 and 21 and the seal 107 for plastifying and/or melting the seal 107.

In further embodiments, the seal 107 can comprise an elastic material. The elastic material can be produced, for example, by an injection molding process or by a polymeric process. The seal 107 can comprise according holes adapted for inserting the ends of the wave guide 17 and the capillary 21 for realizing a preassembly comprising the wave guide 17 and the capillary 21 and the seal 107, wherein the assembly is adapted for being inserted into the recess 79 of the half shell 49. Thereafter, the cover shell 51 can be fit together with the half shell 49. Possibly, the seal 107 can comprise the elastic material, wherein the elastic material comprises a slit adapted for receiving the wave guide 17 and the capillary 21.

Figure 15:
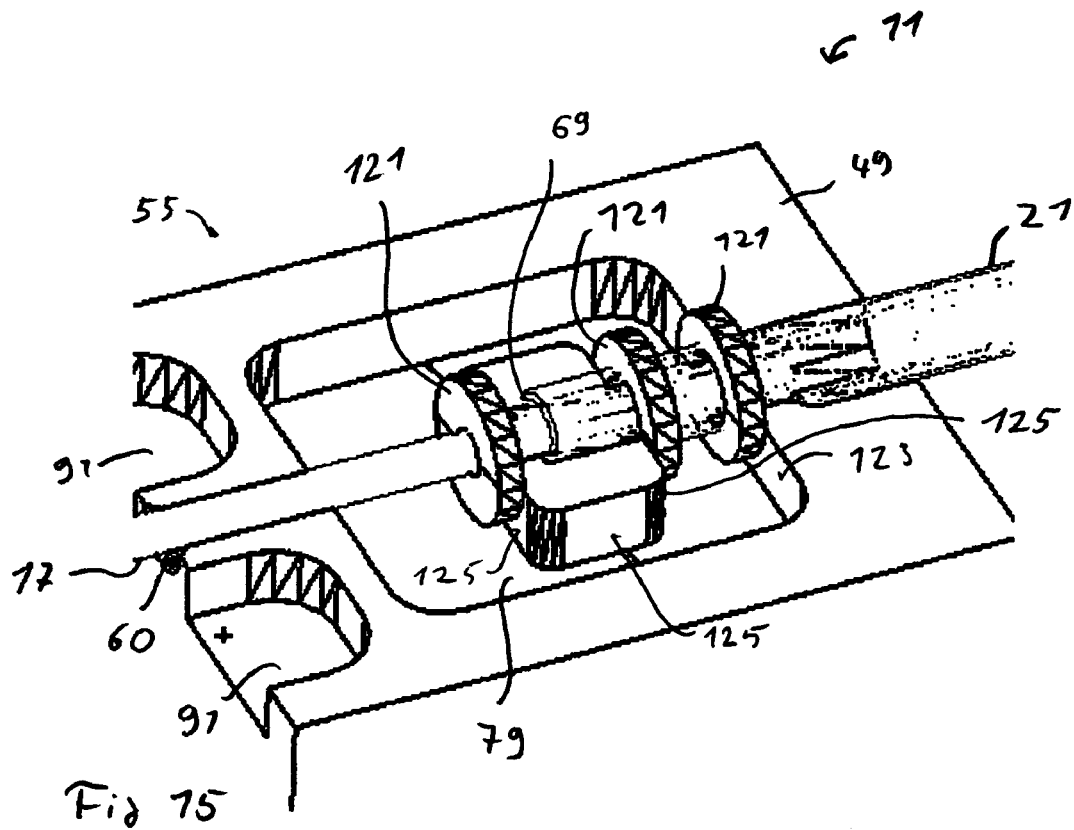
FIG. 15 shows a 3-dimensional detailed view of the half shell of FIG. 6, but additionally with three sealing washers.

FIG. 15 shows a detailed view of the half shell 49 of FIG. 6, but additionally with three sealing washers 121. The washers are fitted to the outer surfaces of the wave guide 17 and the capillary 21, wherein the capillary 21 comprises two washers and the wave guide 17 one. For assembling the wave guide 17 and the capillary 21 with the half shell 49 as shown in FIG. 15, firstly, the capillary 21 can be inserted together with the two preassembled washers into the second groove 63 and the recess 79 of the half shell 49. The two washers 121 of the capillary 21 realize two limit stops, one for an inner surface 123 of the recess 79 and one for an outer surface 125 of the support member 57 of the half shell 49. By this, the capillary 21 can be positioned exactly within the second groove 63 of the half shell 49. Additionally, the wave guide 17 can be inserted into the opening 69 of the capillary 21 until the washer 121 of the wave guide 17 stops at the outer surface 125 of the support member 57 of the half shell 49. Besides this, the washers 121 can realize a low pressure seal.

The support member 57 substantially comprises a cubical shape. In further embodiments, the support member 57 of the half shell 49 can comprise different shapes, for example a round shape or any other shape. The recess 45 or rather the cavity 105 of the half shell 49 and the cover shell 51 substantially comprise a cubical shape. In further embodiments, the cavity 105 can comprise, for example, a cylindrical shape or any other shape.

Figure 16:
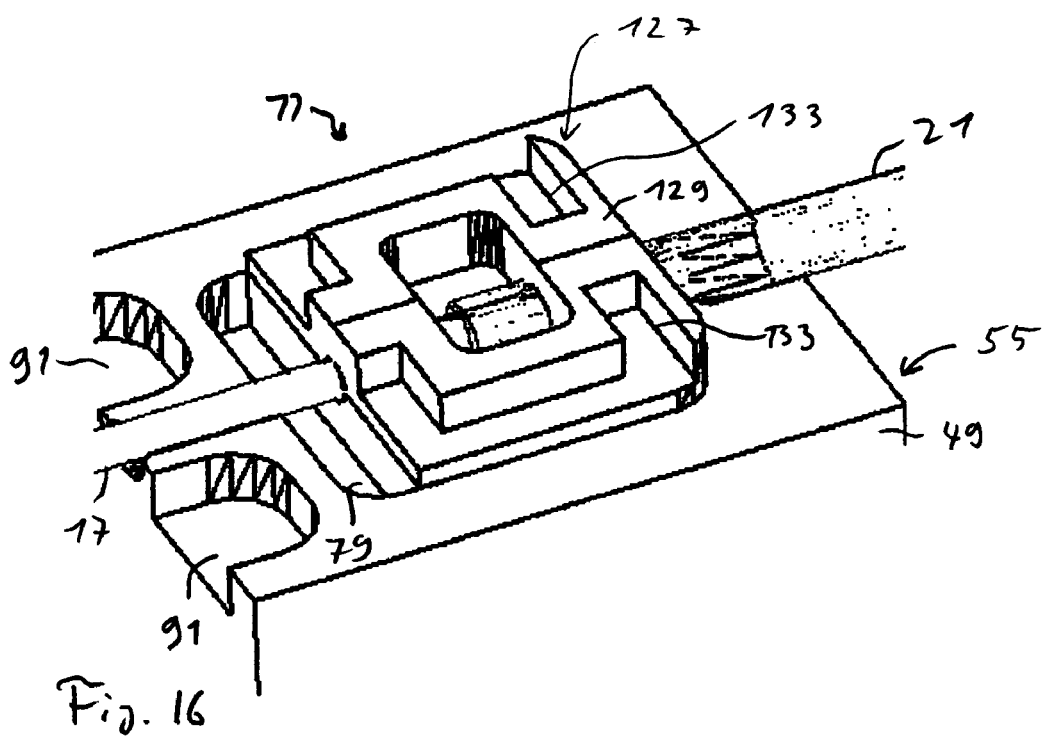
FIG. 16 shows a 3-dimensional detailed view of the half shell of FIG. 6, but additionally with a low pressure seal of a compound seal.
Figure 17:
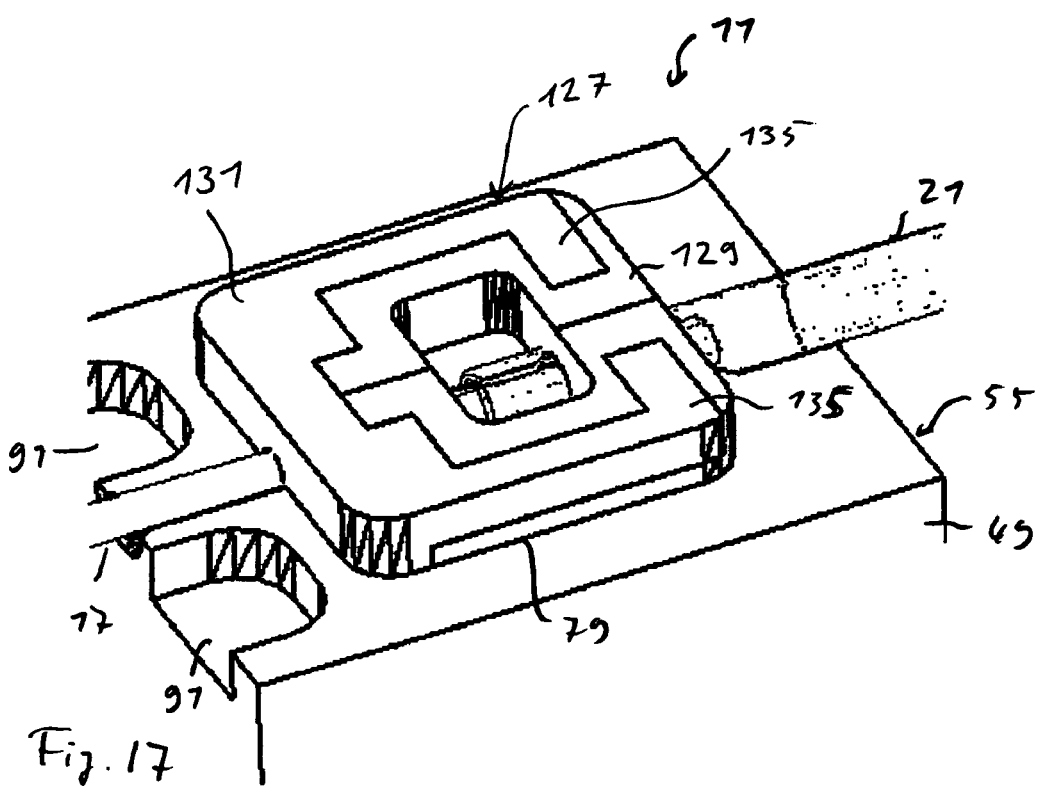
FIG. 17 shows the half shell of FIG. 16, but showing the complete compounded seal comprising the low pressure seal and a high pressure seal.

FIGS. 16 and 17 show a detailed view of the half shell 49 of FIG. 6, but together with a seal 127. The seal 127 comprises a low pressure seal 129 and a high pressure seal 131, wherein FIG. 16 shows the seal 127 without the high pressure seal 131. The low pressure seal 129 and the high pressure seal 131 of the seal 127 are adapted for fitting together. The low pressure seal 129 can comprise an elastomeric and/or a thermoplastic material, wherein said elastomeric and/or a thermoplastic material is adapted to be in contact with the liquid conducted within the capillary 21. The material of the low pressure seal 129 can be inert against strong solvent.

The low pressure seal 129 comprises two recesses 133 adapted for receiving two ribs 135 of the high pressure seal 131 in a form-fitting manner. The high pressure seal 131 can comprise an adhesive, wherein the adhesive has to be protected against strong solvents by the low pressure seal 129 of the seal 127. Therefore, the low pressure seal 129 surrounds the rib 109 provided by the support members 57 of the half shell 49 and the cover shell 51 and surrounds the outer surfaces of the wave guide 17 and the capillary 21 for realizing a sealing contact for the fluid conduits coupled by the coupling 11. For realizing a high pressure seal, the low pressure seal 129 can be surrounded at least partly with the adhesive of the high pressure seal 131 in a form fitting manner. The adhesive can be inserted as liquid into the cavity 105 of the housing 55. Thereafter, the adhesive of the high pressure seal 131 can be hardened.

Figure 18:
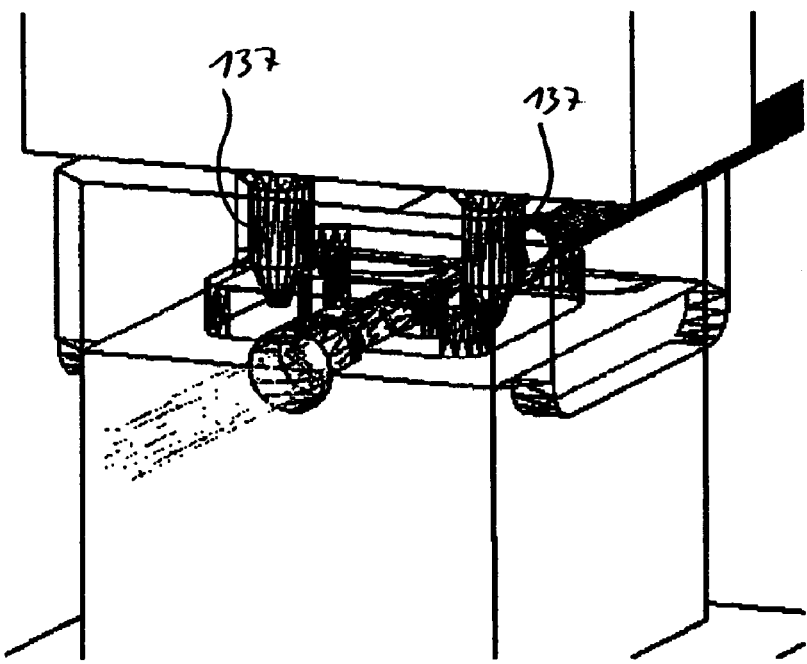
FIG. 18 shows a 3-dimensional front side grid view of a coupling comprising an elastomeric seal pressurized by two pins.

FIG. 18 shows a 3-dimensional grid front side view of the coupling 11, wherein the seal 107 comprises the elastomeric material. The elastomeric material of the seal 107 is pressurized by two pins 137.

Figure 19:
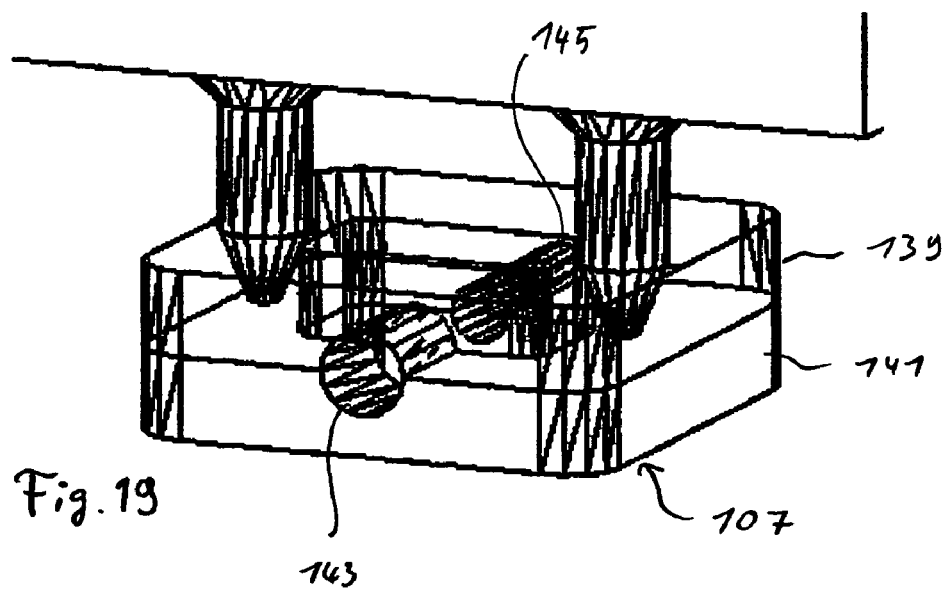
FIG. 19 shows a 3-dimensional detailed front side grid view of the elastomeric seal and the pins of FIG. 18, but simplified by omitting the housing and the conduits of the coupling.

FIG. 19 shows a detailed grid view of the elastomeric seal 107 and the two pins 137 of FIG. 18. FIG. 19 is simplified by omitting the housing 55 and the conduits of the coupling 11. As can be seen in FIG. 19, the seal 107 comprises a top layer 139 and a bottom layer 141. The layers 139 and 141 of the seal 107 are adapted for receiving the wave guide 17 and the capillary 21. Therefore, the layers 139 and 141 of the seal 107 provide a first aperture 143 adapted for receiving the capillary 21 and a second aperture 145 adapted for receiving the wave guide 17. The two pins 137 are inserted into the bores 111 of the holes 53 of the cover shell 51. By this, the two pins 137 can be engaged with the top layer 139 of the seal 107. By this, the seal 107 can be pressurized whereas the inner surfaces of the apertures 143 and 145 can provide a sealing contact with the outer surfaces of the wave guide 17 and the capillary 21. Besides this, the seal 107 is pressed against the surface 125 of the rib 109 and the inner surface 123 of the recesses 45 or rather the surface of the cavity 105 of the half shell 49 and the cover shell 51.

For assembling the coupling 11 comprising the seal 107 as shown in the FIGS. 18 and 19, firstly, the bottom layer 141 can be inserted into the recess 45 of the half shell 49. Thereafter, the capillary 21 can be inserted into the second groove 63 of the half shell 49 and into the aperture 143 of the bottom layer 141 of the seal 107. Thereafter, the wave guide 17 can be inserted into the opening 69 of the capillary 21 by inserting it into the first groove 61 of the half shell 49 and into the second aperture 145 of the bottom layer 141 of the seal 107. Thereafter, the top layer 139 can be fit together with the bottom layer 141 of the seal 107 as can be seen in FIG. 19. Subsequently, the housing 55 can be closed by fitting the cover shell 51 to the half shell 49. Finally, the pins 137 can be inserted into the bores 111 of the cover shell 51 for pressurizing the seal 107 within the cavity 105 of the housing 55.

Possibly, the housing of the coupling can comprise two of said seals and two of said recesses, wherein, for example, each end of the capillary is coupled with one of said seals. By this, a flow cell with just one half shell and one cover shell—comprising said two seals—can be realized. For this purpose, the shells can comprise an additional groove adapted for housing the capillary and an air gap between the groove and the capillary.

Furthermore, a foil can be fed into the recesses or between the shells, for example, for sealing the conduits.

Besides this, the seal can comprise a bore adapted for receiving the capillary and/or the wave guide. Possibly, the seal can comprise slits and/or more than two component parts.

Additionally, at least one of the shells can comprise a cavity ending up in the recess, wherein the cavity provides a flow-off tank, for example, for taking the plastic material during heating. By this, the pressure within the recesses can be balanced.

Besides this, the sealing material can be injected into the housing 55 for providing the seal.

Figure 20:
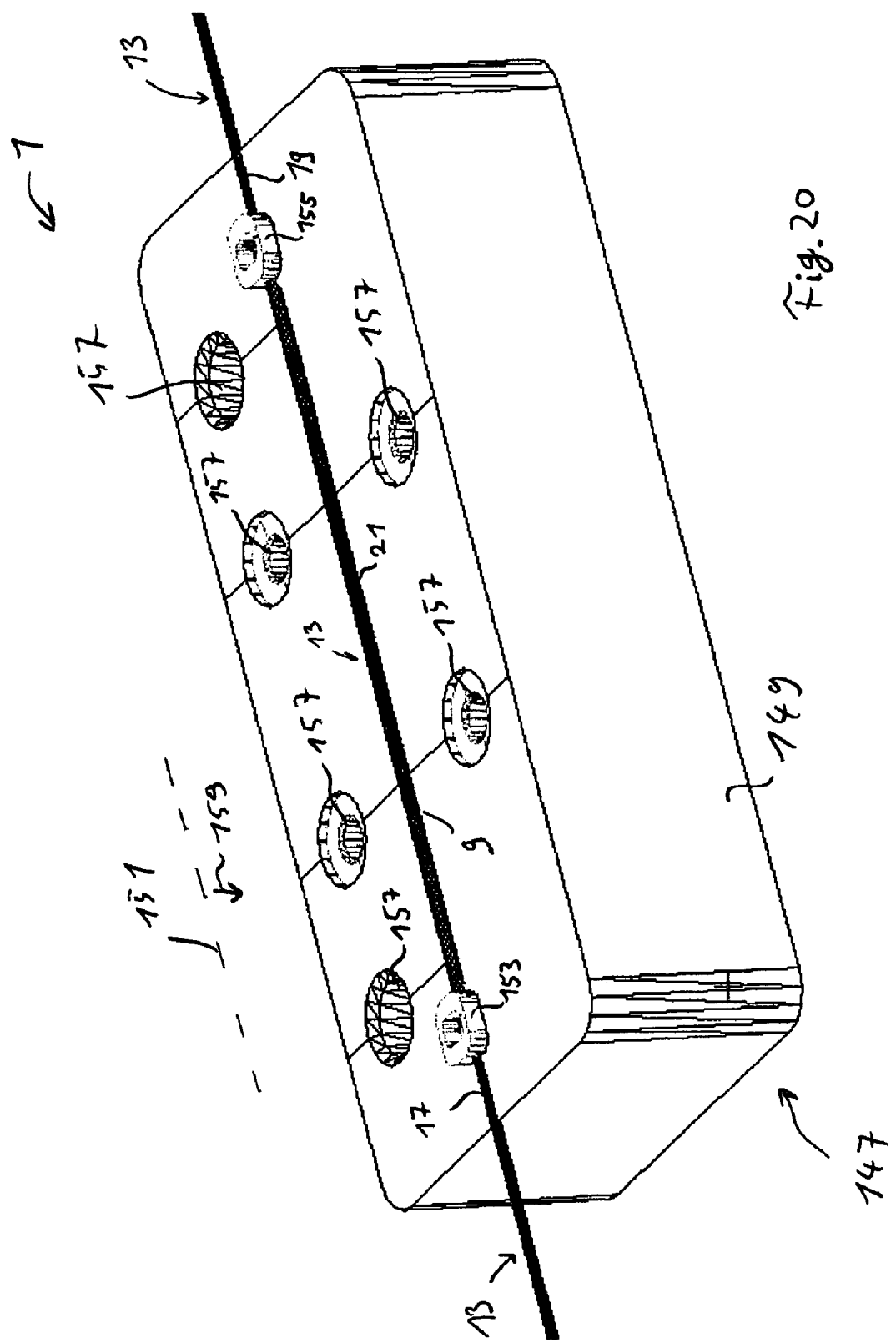
FIG. 20 shows a 3-dimensional top side front view of a flow cell with an integral body.

FIG. 20 shows a 3-dimensional top side front view of a flow cell 1 with an integral body 147. The body 147 comprises a half shell 149 and an according cover shell 151—just indicated with a dashed line. As a difference, the body 147 acts as the housing of the flow cell 1 and can comprise all functional elements of the half shell 49 and the cover shell 51 of the flow cell 1 of the FIG. 1 to 19, for example said rips and said cavity. By this, any additional parts, for example, the supporting plate 5 can be dropped. As a difference, the body 147 can be adapted for receiving a plurality of seals, for example, a first seal 153 and a second seal 155. For assembling the flow cell 1, the shells 149 and/or 151 can be equipped with the capillary 21, the inlet wave guide 17, the outlet wave guide 19, and the first and second seals 153 and 155. Thereafter, the shells 149 and 151 can be assembled together as indicated by an arrow 159 and can be fixed together, for example, by inserting screws into bores 157.

Advantageously, the shells 149 and 151 can be produced in one process step, wherein all necessary structures can be inserted into the shells 149 and 151. After joining the shells 149 and 151, all seals 153 and 155 can be treated together by an according tool, for example, an arrangement of local heating elements adapted for locally heating the body 147 of the flow cell 1.

Figure 21:
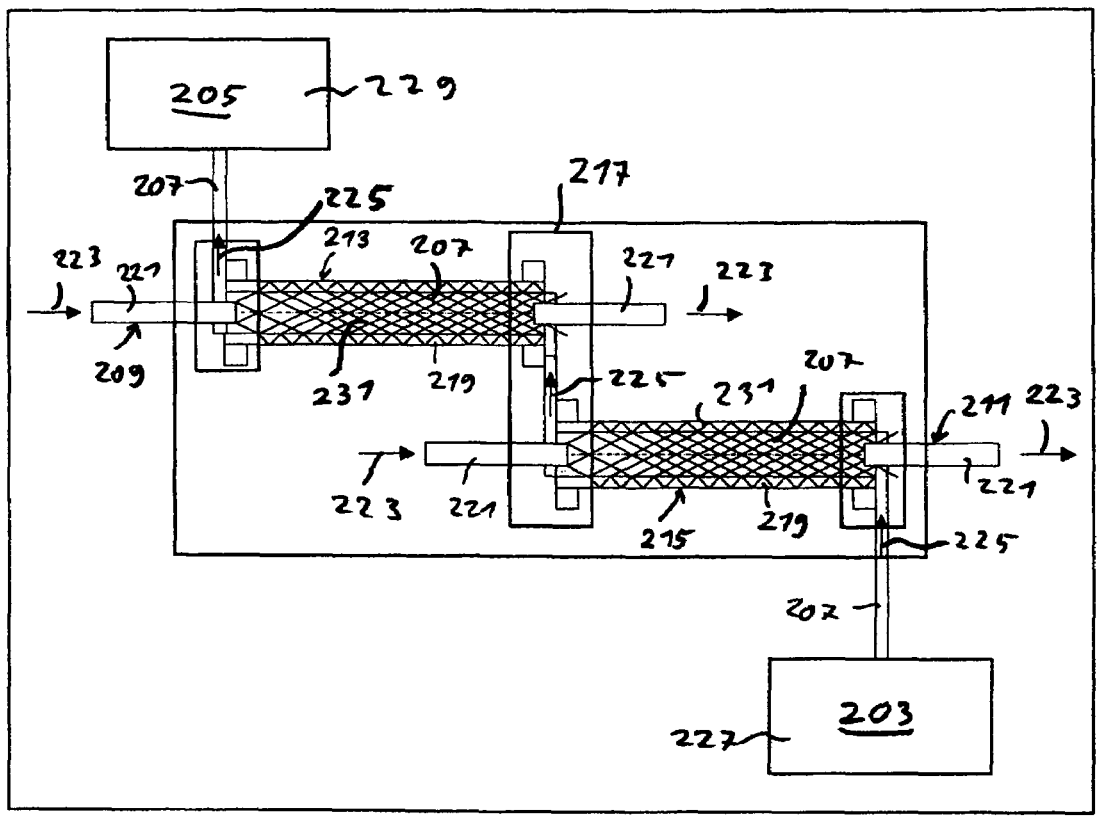
FIG. 21 shows a fluidic system with two flow cells.

FIG. 21 shows a fluidic system 201 comprising a fluid source 203, for example a pump, a nanopump, and/or alike, and a fluid sink 205, for example a waste or a downstream coupled device, for example for analysis purposes.

Between the fluid source 203 and the fluid sink 205, the fluidic system 201 comprises a fluid path 207. The fluid path 207 is coupled with at least one light path 209. Possibly, the fluid path 207 of the fluidic system 201 can be coupled with a second light path 211. The fluid path 207 and the first and second light paths 209 and 211 belong to a first and a second flow cell 213 and 215.

For coupling the fluid path 207 and the first and second light paths 209 and 211, the fluidic system 201 comprises at least one coupling 217. The coupling 217 can be realized according to one of the couplings according to the Figures above.

Each of the flow cells 213 and 215 comprises a capillary 219 and comprises a wave guide 221. The capillaries 219 of the first and second flow cells 213 and 215 are adapted for conducting a fluid, for example, a fluid comprising a sample, for example, a sample dissolved in a liquid. For analyzing the sample of the fluid, the fluid can be irradiated by the wave guides 221 of the light paths 209 of the first and second flow cells 213 and 215. For measuring the amount of light guided through the fluid sample, the light paths 209 can be connected to not shown light detectors.

Furthermore, the coupling/s 217 can comprise a plurality of communicating branches, for example, for coupling the capillaries 219, the wave guides 213, and/or according supplying or rather draining conduits to each other.

The direction of the light guided though the light paths 209 of the first and second flow cells 213 and 215 are indicated by arrows 223. The direction of the fluid guided though the fluid paths 207 of the first and second flow cells 213 and 215 are indicated by arrows 225. Besides this, different beams of the light paths 209 are indicated by lines 231.

The capillaries 219 of the first and second flow cells 213 and 215 can comprise a transparent material, for example glass, quartz glass, and/or alike, wherein within the walls of the capillaries total reflection can occur as shown by the beams as indicated by the lines 231 of FIG. 21.

The fluid source 203 can comprise a separating device 227 and/or can be coupled with such a device. Besides this, the fluid sink 205 can comprise an analyzing device 229, for example, a mass spectrograph. The fluidic system 201 can be realized as an integrated system for analysis purposes, for example as a integrated system commercially available, for example, a chromatographic system (LC), a high performance liquid chromatographic (HPLC) system, an HPLC arrangement comprising a chip and an mass spectrograph (MS), a high throughput LC/MS system, a purification system, a micro fraction collection/spotting system, a system adapted for identifying proteins, a system comprising a GPC/SEC column, a nanoflow LC system, and/or a multidimensional LC system adapted for separation of protein digests.

The fluidic system 201 can be adapted for analyzing liquid. More specifically, the fluidic system 201 can be adapted for executing at least one microfluidic process, for example an electrophoresis and/or a liquid chromatographic process, for example a high performance liquid chromatographic process (HPLC). Therefore, the fluidic system 201 can be coupled to a liquid delivery system, in particular to a pump, and/or to a power source. For analyzing liquid or rather one or more components within the liquid, the fluidic system 201 can comprise a detection area, such as an optical detection area and/or an electrical detection area being arranged close to a flow path within the fluidic system 201. Otherwise, the fluidic system 201 can be coupled to a laboratory apparatus, for example to a mass spectrometer, for analyzing the liquid. For executing an electrophoresis, the flow path can comprise a gel. Besides this, the fluidic system can be a component part of a laboratory arrangement.

It is to be understood, that this invention is not limited to the particular component parts of the devices described or to process steps of the methods described as such devices and methods may vary. It is also to be understood, that different features as described in different embodiments, for example illustrated with different Fig., may be combined to new embodiments. It is finally to be understood, that the terminology used herein is for the purposes of describing particular embodiments only and it is not intended to be limiting. It must be noted, that as used in the specification and the appended claims, the singular forms of "a", "an", and "the" include plural referents until the context clearly dictates otherwise. Thus, for example, the reference to "a housing part" or "a fluid path" may include two or more such functional elements.

What is claimed is:

1. A coupling comprising:
a capillary for conducting a fluid,
a conduit for one of supplying the capillary with fluid and draining the capillary of fluid,
a wave guide for conducting light, the wave guide having an end that is inserted into an end of the capillary to define an opening therebetween,
a housing comprising:
a first aperture that receives the wave guide into the housing,
a second aperture that receives the capillary into the housing,
a recess defined in the housing that receives the wave guide and the capillary,
a support member in the recess, the support member positions and supports the wave guide and the capillary in the recess, and comprises a bore that fluidically couples the conduit to the opening, and
a seal within the recess that seals the coupling between the conduit and the opening to prevent fluid leakage therefrom.

2. The coupling of claim 1, wherein:
the housing comprises:
a half shell having a first support member, and
a cover shell having a second support member, the cover shell being attached to the half shell with the first support member and the second support member facing each other to define the support member in recess in the housing, and wherein the seal surrounds the support member.

3. The coupling of claim 2, wherein the first aperture in the housing is defined by respective first grooves in the half shell and the cover shell, and the second aperture in the housing is defined by respective second grooves in the half shell and the cover shell.

4. The coupling of claim 1, wherein the housing further comprises:

an undercut in a surface of the housing defining the recess, the undercut being filled by the seal so that the seal is secured in place in the recess.

5. The coupling of claim 2, wherein:

one of the first support member and the second support member is attached to the respective shell via a spring mount.

6. The coupling of claim 2, wherein at least one of the shells comprises a limit stop that positions the capillary at a predetermined position within the housing.

7. The coupling of claim 1, wherein the wave guide comprises an optical element including one of a window and a glass rod.

8. The coupling of claim 1, wherein:

the end of the wave guide inserted into the end of the capillary is coaxial with the end of the capillary.

9. The coupling of claim 2, wherein the seal comprises one of:

a plastic material that was heated to a molten state and subsequently solidified, and the housing comprises a cavity that allows excess molten plastic to flow out of the recess, an elastomeric material is pressurized by at least one pin inserted into the recess through a bore in one of the half shell and the cover shell, a low pressure seal made of one of an elastomeric material, a soft thermoplastic material, and Teflon, a low pressure seal and at least one washer, a low pressure seal and a high pressure seal, the high pressure seal being made of a high pressure resistant seal material including one of an adhesive, a thermoplastic material, a low temperature alloy and a low temperature metal, and a low pressure seal and a high pressure seal made of adhesive, the low pressure seal being in contact with the fluid and protects the adhesive against any contact with the fluid.

10. A fluidic system comprising:

a capillary for conducting a fluid, at least two couplings, each coupling comprising:

a conduit for one of supplying the capillary with fluid and draining the capillary of fluid, a wave guide for conducting light, the wave guide having an end that is inserted into an end of the capillary to define an opening therebetween, a housing comprising:

a first aperture that receives the wave guide into the housing, a second aperture that receives the capillary into the housing, a recess defined in the housing that receives the wave guide and the capillary, a support member in the recess, the support member positions and supports the wave guide and the capillary in the recess, and comprises a bore that fluidically couples the conduit to the opening, and a seal within the recess that seals the coupling between the conduit and the opening to prevent fluid leakage therefrom.

11. The fluidic system of claim 10, further comprising:

a supporting plate that supports the capillary and couplings.

12. The fluidic system of claim 10, further comprising a fluid delivery system, and a separation device that separates components of a fluid delivered by the fluid delivery system before the fluid is supplied to the capillary via one of the conduits.

13. The fluidic system of claim 10, wherein said fluidic system comprises at least one of:

a chromatographic system (LC), a high performance liquid chromatographic (HPLC) system, an HPLC arrangement comprising a chip and an mass spectrograph (MS), a high throughput LC/MS system, a purification system, a micro fraction collection/spoiling system, a system adapted for identifying proteins, a system comprising a GPC/SEC column, a nanoflow LC system, and a multidimensional LC system adapted for separation of protein digests.

* * * * *